United States Patent
Das

(10) Patent No.: US 11,549,888 B2
(45) Date of Patent: Jan. 10, 2023

(54) METHOD FOR MEASURING MONOCHLORAMINE IN SEAWATER

(71) Applicant: Hach Company, Loveland, CO (US)

(72) Inventor: Amit Das, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 149 days.

(21) Appl. No.: 16/592,339

(22) Filed: Oct. 3, 2019

(65) Prior Publication Data

US 2021/0102930 A1 Apr. 8, 2021

(51) Int. Cl.
*G01N 21/64* (2006.01)
*G01N 21/77* (2006.01)
(Continued)

(52) U.S. Cl.
CPC .......... *G01N 21/643* (2013.01); *G01N 21/64* (2013.01); *G01N 21/77* (2013.01); *G01N 31/22* (2013.01); *G01N 33/18* (2013.01); *C07D 311/16* (2013.01); *G01N 33/182* (2013.01); *G01N 2021/6439* (2013.01); *G01N 2021/7786* (2013.01); *Y10T 436/193333* (2015.01)

(58) Field of Classification Search
CPC ........ Y10T 436/19; Y10T 436/193333; G01N 21/64; G01N 21/6428; G01N 21/643; G01N 21/77; G01N 2021/6439; G01N 2021/6443; G01N 2021/7786; G01N 33/18; G01N 33/182
See application file for complete search history.

(56) References Cited

U.S. PATENT DOCUMENTS

| 5,702,684 A | * | 12/1997 | McCoy | ................. A01N 61/00 210/745 |
| 11,422,093 B2 | * | 8/2022 | Das | ....................... G01N 31/22 |

(Continued)

FOREIGN PATENT DOCUMENTS

| CN | 108409697 A | * | 8/2018 | .......... C07D 311/16 |
| JP | S6366466 A | | 3/1988 | |

OTHER PUBLICATIONS

Wang, X. et al. "A highly selective fluorescent probe for the detection of hypochlorous acid in tap water and living cells," Spectrochimica Acta Part A: Molecular and Biomolecular Spectroscopy 203 (2018) 415-120; Supplementary data only. Available online Jun. 3, 2018 (Year: 2018).*

(Continued)

*Primary Examiner* — Jennifer Wecker
*Assistant Examiner* — Michelle Adams
(74) *Attorney, Agent, or Firm* — Ference & Associates LLC

(57) ABSTRACT

An embodiment provides a method for measuring total chlorine in a seawater sample, including: preparing a thiocarbamate-based indicator; introducing the thiocarbamate-based indicator to a seawater sample, wherein the seawater sample contains an amount of total chlorine; adding an additive to the seawater sample, wherein the additive accelerates the reaction rate between the thiocarbamate-based indicator and total chlorine and causes a change in fluorescence of the seawater sample; and measuring the amount of total chlorine in the seawater sample by measuring an intensity of the fluorescence. Other aspects are described and claimed.

8 Claims, 4 Drawing Sheets

(51) Int. Cl.
*G01N 33/18* (2006.01)
*G01N 31/22* (2006.01)
*C07D 311/16* (2006.01)

(56) References Cited

U.S. PATENT DOCUMENTS

2008/0149485 A1* 6/2008 Childers ............ G01N 33/1846
 204/555
2009/0320570 A1* 12/2009 Wiese ................ G01N 33/0013
 73/61.43
2010/0204185 A1 8/2010 Hecht et al.

OTHER PUBLICATIONS

Harp, D.L. "Current Technology of Chlorine Analysis for Water and Wastewater," Technical Information Series—Booklet No. 17. Hach Company, 2002. (Year: 2002).*

Engelhardt, T.L. et al. "Chlorination, Chloramination and Chlorine Measurement," Hach Company, 2015 (Year: 2015).*

International Searching Authority, Notification of Transmittal of the International Search Report and the Written Opinion of the International Searching Authority, or the Declaration, dated Dec. 21, 2020, pp. 15.

"Jin Lei et al: "A novel coumarin-based fluorescent probe with fine selectivity and sensitivity for hypochlorite and its application in cell imaging"", TALANTA, vol. 202, Apr. 29, 2019 (Apr. 29, 2019), pp. 190-197.

"Xiao Wang et al: "A Highly selective fluorescent probe for the detection of hypochlorous acid in tap water and living cell s", ", Spectrochimi CA Acta. Part A: Molecular and Biomolecular Spectroscopy, vol. 203, Oct. 1, 2018 (Oct. 1, 2018), pp. 415-420.

"Zhu Baocun et al: "A fast-response, highly specific fluorescent probe for the detection of picomolar hypochlorous acid and its bioimaging applications "", Sensors and Actuators B: Chemical, Elsevier BV, NL, vol. 263, Feb. 12, 2018 (Feb. 12, 2018), pp. 103-108.

"Zhu Baocun et al: "A highly specific and ultrasensitive two-photon fluorescent probe for imaging native hypochlorous acid in living cells "", Sensors and Actuators B: Chemical, Elsevier BV, NL, vol. 269, Apr. 26, 2018 (Apr. 26, 2018), pp. 1-7.

* cited by examiner

METHOD FOR MEASURING MONOCHLORAMINE IN SEAWATER

BACKGROUND

This application relates generally to measuring chlorine in aqueous or liquid samples, and, more particularly, to the measurement of chlorine in seawater.

Ensuring water quality is critical in a number of industries such as pharmaceuticals and other manufacturing fields. Additionally, ensuring water quality is critical to the health and well-being of humans, animals, and plants which are reliant on the water for survival. One element that is typically measured is chlorine. Too much chlorine in water can be harmful to humans, animals, and aquatic life. Therefore, detecting the presence and concentration of chlorine in seawater, water, or other liquid solutions is vital.

BRIEF SUMMARY

In summary, one embodiment provides a method for measuring total chlorine in a seawater sample, comprising: preparing a thiocarbamate-based indicator; introducing the thiocarbamate-based indicator to a seawater sample, wherein the seawater sample contains an amount of total chlorine; adding an additive to the seawater sample, wherein the additive accelerates the reaction rate between the thiocarbamate-based indicator and total chlorine and causes a change in fluorescence of the seawater sample; and measuring the amount of total chlorine in the seawater sample by measuring an intensity of the fluorescence.

Another embodiment provides a measurement device for measuring total chlorine in a seawater sample, comprising: at least one measurement chamber; a processor; and a memory storing instructions executable by the processor to: prepare a thiocarbamate-based indicator; introduce the thiocarbamate-based indicator to a seawater sample, wherein the seawater sample contains an amount of total chlorine; add an additive to the seawater sample, wherein the additive accelerates the reaction rate between the thiocarbamate-based indicator and total chlorine and causes a change in fluorescence of the seawater sample; and measure the amount of total chlorine in the seawater sample by measuring an intensity of the fluorescence.

A further embodiment provides a method for measuring total chlorine in a seawater sample, comprising: preparing a thiocarbamate-based indicator; introducing the thiocarbamate-based indicator to a seawater sample, wherein the seawater sample contains an amount of total chlorine; adding potassium iodide to the seawater sample, wherein the potassium iodide accelerates the reaction rate between the thiocarbamate-based indicator and total chlorine and causes a change in fluorescence of the seawater sample, wherein the potassium iodide forms potassium triiodide based upon a reaction between the potassium iodide and the total chlorine; and measuring the amount of total chlorine in the seawater sample by measuring an intensity of the fluorescence.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
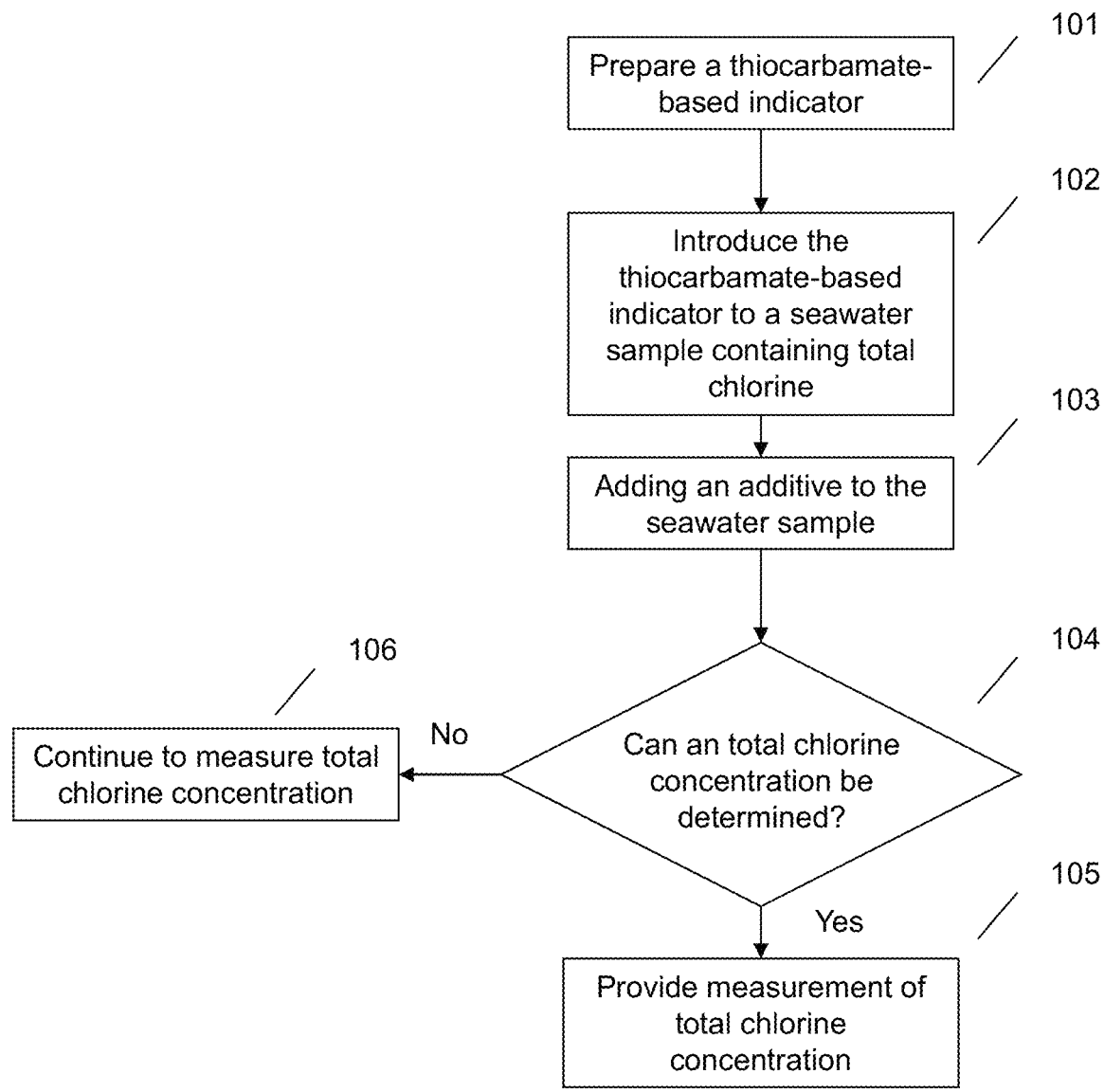
FIG. 1 illustrates a flow diagram of an example total chlorine measuring system for a seawater sample.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional methods of chlorine measurement in water may have some limitations. For example, chlorine measurement may be used to determine the quality of water. High concentrations of chlorine may be harmful to animals, humans, and/or plants. Accordingly, as another example, a user or entity may want the chlorine in a body of water to be under a particular threshold, therefore, the user may measure the chlorine in order to determine if the amount of chlorine is under that threshold.

A standard for free and total chlorine measurement in water is DPD (N,N-diethyl-p-phenylenediamine) colorimetric detection. Total chlorine is the total amount of chlorine in the water including the chlorine that has reacted with nitrogen compounds in the water. In the absence of iodide ion, free chlorine reacts quickly with DPD indicator to produce a red color, whereas chloramines react more slowly. If a small amount of iodide ion is added, chloramines also react to produce color, yielding total chlorine concentration. Absorbance (for example, at 515 nm) may be spectrophotometrically measured and compared to a series of standards, using a graph or a regression analysis calculation to determine free and/or total chlorine concentration.

As set forth above, free chlorine reacts very quickly with DPD while the chloramine species (for example, monochloramine and dichloramine) react more slowly. In attempting to measure free chlorine, the presence of "interfering" species such as monochloramine may produce inaccurate readings. For greatest accuracy, it is typically recommended that the free chlorine measurement using DPD should be made quickly (that is, before the interfering species can react to any significant degree).

Current methods, systems and kits for free chlorine measurement using the DPD colorimetric test are limited because the presence of chloramines can introduce significant errors in free chlorine measurements. Once again, if additional reagents are used to prevent interferences, then additional steps and/or toxic and expensive chemicals are required. Further, the traditional DPD colorimetric test does not allow monochloramine concentrations to be measured directly.

Accordingly, an embodiment provides a system and method for measuring chlorine in a seawater sample. The seawater sample may be drawn from a ballast system in a ship. For example, ballast water may be treated with a chlorine based method, and the total chlorine levels may need to be returned to low enough levels prior to de-ballasting the water back into the environment. In an embodiment, the method may not use traditional DPD chemistry. In an embodiment, the method may detect chlorine in concentrations in about the range of 0 to 50 parts per million (ppm). In an embodiment, the method may use a fluorometric method. The indicator to give a fluorescent signal may be a thiocarbamate derivative. The thiocarbamate derivative may be a derivative of 7-hydroxy coumarin. The thiocarbamate may be an umbelliferone thiocarbamate. An additive may be added to the method. The additive may accelerate the completion time of a reaction. The additive may be potassium iodide (KI). In an embodiment, the fluorescence may be correlated to the detection of monochloramine. In an embodiment, the fluorescence may be correlated to total chlorine in seawater. A buffer such as phosphate buffer may be added. In an embodiment, the pH of a solution may be adjusted to activate the reporter or indicator molecule. The pH may be adjusted to about pH 7.0.

The illustrated example embodiments will be best understood by reference to the figures. The following description is intended only by way of example, and simply illustrates certain example embodiments.

Referring to FIG. 1, an example system and method for detection of total chlorine in a seawater sample is illustrated. In an embodiment, a thiocarbamate-based indicator may be prepared. The thiocarbamate-based indicator may be introduced to a seawater sample containing mono chloramine, chlorine, or total chlorine. In an embodiment, an additive may be added. The additive may be potassium iodide (KI). The additive may accelerate a reaction in seawater. In an embodiment, the thiocarbamate-based indicator in the presence of monochloramine or total chlorine may cause a change in fluorescence intensity of the thiocarbamate indicator. The change of fluorescent intensity may be correlated to a concentration of monochloramine or total chlorine in the solution.

Figure 2:
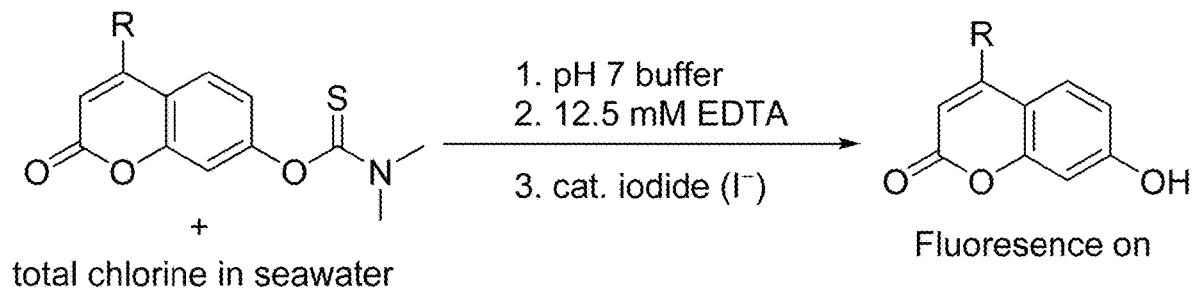
FIG. 2 illustrates a chemical equation of an example thiocarbamate-based indicator for detection of total chlorine.

At 101, in an embodiment, a thiocarbamate-based indicator may be prepared. The thiocarbamate may be a thiocarbamate derivative of hydroxy coumarin. In an embodiment, the thiocarbamate indicator may be methylumbelliferone thiocarbamate or umbelliferone thiocarbamate-based. Referring to FIG. 2, an example reaction of the thiocarbamate-based indicator is illustrated. In an embodiment, the thiocarbamate-based indicator may detect monochloramine or total chlorine in the range of 0-50 ppm. The range is exemplary, a range may be determined based upon the need to return chlorine levels to a suitable level for de-ballasting of water back into the environment.

At 102, in an embodiment, the thiocarbamate-based indicator may be introduced into a seawater sample. The seawater sample may contain monochloramine. The solution may be a seawater sample which may include a sample from a natural body of water, a holding tank, a processing tank, a pipe, a ballast water system, a ballast water treatment system, sea chest, ballast tank, or the like. The solution may be in a continuous flow, a standing volume of liquid, or any combination thereof. In one embodiment, the seawater sample may be introduced to the thiocarbamate-based indicator, for example, a test chamber of the measurement device. Introduction of the seawater sample into the measurement device may include placing or introducing the seawater sample into a test chamber manually by a user or using a mechanical means, for example, gravity flow, a pump, pressure, fluid flow, or the like. For example, a water sample for chlorine testing may be introduced to a measurement or test chamber using a pump. In an embodiment, valves or the like may control the influx and efflux of the solution into or out of the one or more chambers, if present.

Additionally or alternatively, the measurement device may be present or introduced in a volume of the seawater sample. The measurement device is then exposed to the volume of seawater sample where it can perform measurements. The system may be a flow-through system in which a solution and/or reagents are automatically mixed and measured. Once the sample is in contact with the measurement system, the system may measure the chlorine of the sample, as discussed in further detail herein. In an embodiment, the measurement device may include one or more chambers in which the one or more method steps may be performed.

At 103, in an embodiment, an additive may be added to the seawater sample. The additive may be potassium iodide (KI). The additive may accelerate the reaction. The additive may accelerate the reaction of the thiocarbamate indicator and the monochloramine. For example, a thiocarbamate-based indicator may take 10 hours or more to react with monochloramine. The additive may reduce the reaction time and/or accelerate the reaction of the thiocarbamate indicator with monochloramine to approximately 30 seconds. In an embodiment, the pH of the solution may be controlled. Additionally or alternatively, chlorine or chloramine may be added to the solution. In an embodiment, the thiocarbamate-based indicator in the presence of monochloramine may "turn-on" the fluorescent properties of the thiocarbamate-based indicator.

In an embodiment, the pH of the solution may be maintained at a neutral pH. For example, the pH may be adjusted or titrated to around a pH of 7.0. The thiocarbamate-based indicator may be approximately 5 µM. In an embodiment, a buffer may be added. The buffer may be a phosphate buffer. The phosphate buffer concentration may be about 75 mM. In an embodiment, the potassium iodide may be approximately 30-40 µM. Saline may be added in the concentration range of 0-50 mM. An approximate range of detection of total chlorine is between 0-50 ppm.

In an embodiment, a co-solvent may be added to the seawater sample. The co-solvent may allow the thiocarbamate indicator to be more soluble in seawater. The co-solvent may be selected based upon environmentally friendly, or "green", considerations. The co-solvent may be a low molecular weight molecule. In an embodiment, the co-solvent may comprise poly(ethylene glycol), poly(ethylene glycol)dimethyl ether, poly(ethylene glycol)methyl ether, or the like. In an embodiment, the co-solvent may be a mixture of the co-solvents contemplated. The co-solvent may be used at a concentration less than or equal to 5% of the seawater sample volume. The co-solvent may have a high boiling point. The boiling point may be greater than 250 degrees Celsius. The co-solvent may have a high flash point. The flash point may be greater than 200 degrees Celsius. The high boiling point and flash point temperature may be selected for the particular application, environment, or the like.

Figure 3:
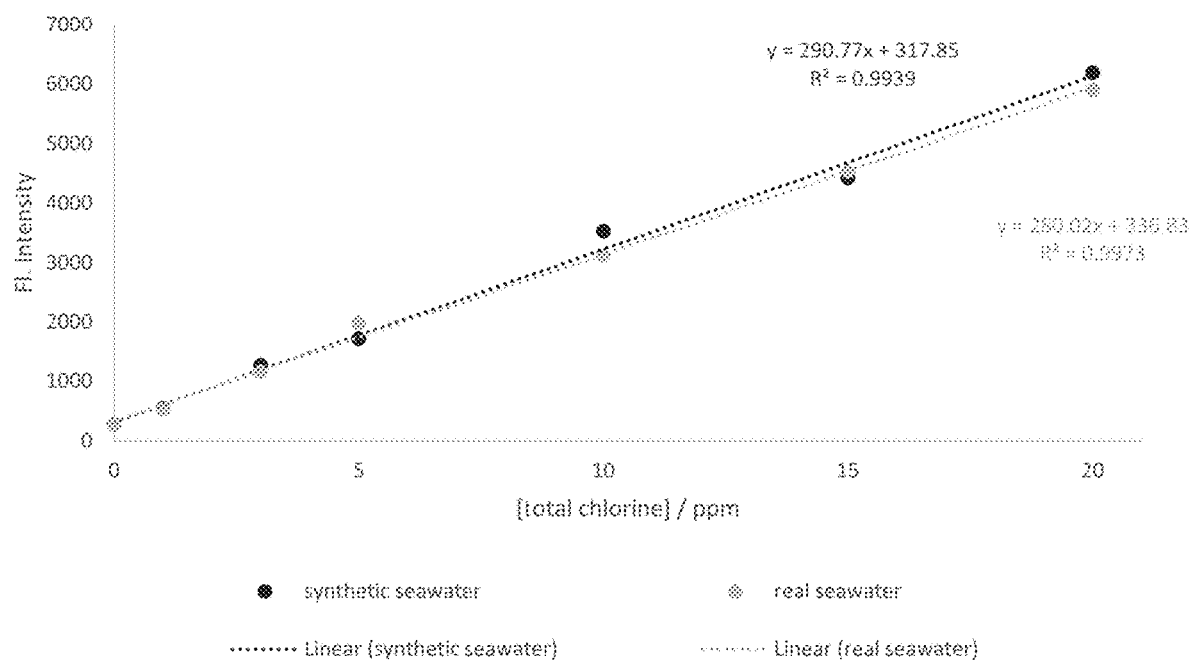
FIG. 3 illustrates an example fluorescence intensity measurement using a thiocarbamate-based indicator.

At 104, in an embodiment, the system and method may determine if a monochloramine concentration may be determined. In an embodiment, the presence of monochloramine or total chlorine in a seawater sample may cause an increase in fluorescence intensity of the thiocarbamate-based indicator. Examples of this increase in fluorescence intensity and dose response curves for a thiocarbamate-based indicator may be illustrated in FIG. 3. An embodiment, of fluorescence intensity is plotted over total chlorine (in ppm). Synthetic seawater versus real seawater is illustrated. For this example the synthetic seawater comprised: 500 mM sodium, 50 mM magnesium, 10 mM potassium, 10 mM calcium, 575 mM chloride, sulfate 30 mM, and bromide 1 mM. In an embodiment, the thiocarbamate-based indicator comprised 0.22 mM at a near neutral pH. The pH may be a pH around 7.0. A phosphate buffer may be added. A solution of the thiocarbamate-based indicator may be prepared in PEG 200 and added to the seawater sample keeping the PEG 200 volume of less than or equal to 5% of the sample volume. PEG 200 was selected as it has greater than 200 degree Celsius boiling point and flash point. The high flash point may be useful for ballast water applications. In an embodiment EDTA may be added. The concentration of the EDTA may be 12.5 mM. The EDTA may prevent the formation of a metal phosphate by complexation. Potassium iodide may be added as a catalytic additive. The indicator may be used in a total chlorine range of 0-20 ppm as illustrated. However, the indicator is effective up to and beyond 50 ppm.

Therefore, the fluorescence intensity, of a solution containing monochloramine or total chlorine may be correlated to the concentration of the monochloramine or total chlorine in the aqueous solution. Fluorescence curves may be generated for a range of concentrations, for different thiocarbamate-based indicators, for any different condition that may affect absorption or fluorescence values (e.g., temperature, sample content, turbidity, viscosity, measurement apparatus, aqueous sample chamber, etc.), or the like.

Alternatively or additionally, monochloramine or total chlorine concentration measurement may be at periodic intervals set by the user or preprogrammed frequencies in the device. Measurement by a device allows for real time data with very little human involvement in the measurement process. Cleaning of the fluorometric chamber may be required at an unspecified time interval. A programmed calibration curve may be entered into the device.

A chamber, vessel, cell, chamber, or the like may contain a seawater sample, at least one thiocarbamate-based indicator, and associated reagents such as buffers and/or additives. A device may contain one or more bottles of reagents which contain necessary reagents. The reagents contained in the one or more bottles may be pump fed or gravity fed. The flow of the reagents may be metered to ensure proper volume delivery to the measurement cell. The seawater sample may be fed through a pressured inlet, a vessel, or the like. The seawater sample may be introduced into the measurement chamber by a pump or gravity fed. The sampling device may be in series or parallel to an aqueous flow. The device may have a system to ensure proper mixing of the aqueous sample, thiocarbamate-based indicator, and related reagents.

The fluorescent intensity or total chlorine concentration may be an output upon a device in the form of a display, printing, storage, audio, haptic feedback, or the like. Alternatively or additionally, the output may be sent to another device through wired, wireless, fiber optic, Bluetooth®, near field communication, or the like. An embodiment may use an alarm to warn of a measurement or concentration outside acceptable levels. An embodiment may use a system to shut down water output or shunt water from sources with unacceptable levels of an analyte. For example, an analyte measuring device may use a relay coupled to an electrically actuated valve, or the like.

At 106, in an embodiment, if a concentration of chlorine cannot be determined, the system may continue to measure total chlorine and/or fluorescence intensity. Additionally or alternatively, the system may output an alarm, log an event, or the like.

If a concentration of total chlorine can be determined, the system may provide a measurement of total chlorine concentration at 105. The system may connect to a communication network. The system may alert a user or a network. This alert may occur whether a total chlorine measurement is determined or not. An alert may be in a form of audio, visual, data, storing the data to a memory device, sending the output through a connected or wireless system, printing the output or the like. The system may log information such as the measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a total chlorine concentration reaches a threshold. Alarms or logs may be analyzed in real-time, stored for later use, or any combination thereof.

The various embodiments described herein thus represent a technical improvement to conventional chlorine measurement techniques. Using the techniques as described herein, an embodiment may use a thiocarbamate-based indicator to measure monochloramine in solution. This is in contrast to DPD chemistry with limitations mentioned above. Such techniques provide a faster and more accurate method for measuring chlorine in an aqueous or liquid solution. The various embodiments described herein thus represent a technical improvement to conventional ballast water treatment techniques. Using the techniques as described herein, an embodiment may use a method and device to measure total chlorine concentration in ballast water. This is in contrast to conventional methods with limitations mentioned above. Such techniques provide a better method to treat ballast water and reduce levels of chlorine to a de-ballast port.

Figure 4:
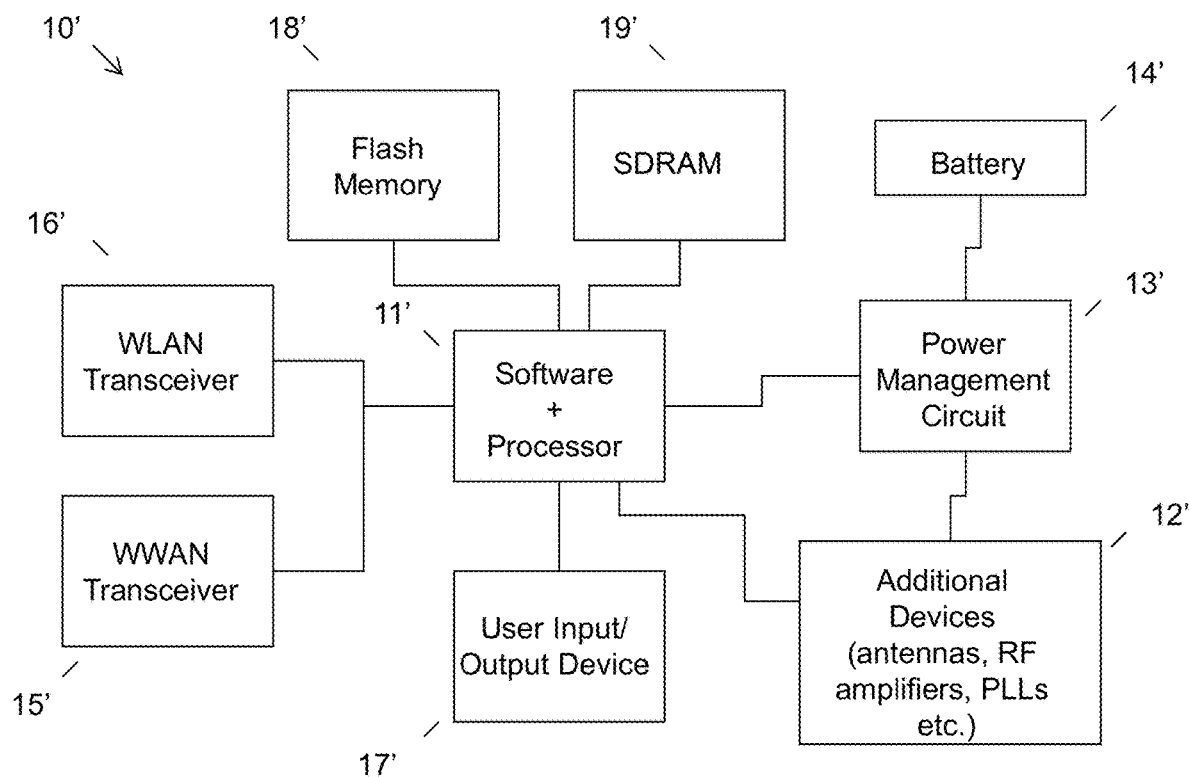
FIG. 4 illustrates an example of computer circuitry.

While various other circuits, circuitry or components may be utilized in information handling devices, with regard to an instrument for total chlorine measurement in seawater according to any one of the various embodiments described herein, an example is illustrated in FIG. 4. Device circuitry 10' may include a measurement system on a chip design found, for example, a particular computing platform (e.g., mobile computing, desktop computing, etc.) Software and processor(s) are combined in a single chip 11'. Processors comprise internal arithmetic units, registers, cache memory, busses, I/O ports, etc., as is well known in the art. Internal busses and the like depend on different vendors, but essentially all the peripheral devices (12') may attach to a single chip 11'. The circuitry 10' combines the processor, memory control, and I/O controller hub all into a single chip 11'. Also, systems 10' of this type do not typically use SATA or PCI or LPC. Common interfaces, for example, include SDIO and I2C.

There are power management chip(s) 13', e.g., a battery management unit, BMU, which manage power as supplied, for example, via a rechargeable battery 14', which may be recharged by a connection to a power source (not shown). In at least one design, a single chip, such as 11', is used to supply BIOS like functionality and DRAM memory.

System 10' typically includes one or more of a WWAN transceiver 15' and a WLAN transceiver 16' for connecting to various networks, such as telecommunications networks and wireless Internet devices, e.g., access points. Additionally, devices 12' are commonly included, e.g., a transmit and receive antenna, oscillators, PLLs, etc. System 10' includes input/output devices 17' for data input and display/rendering (e.g., a computing location located away from the single beam system that is easily accessible by a user). System 10' also typically includes various memory devices, for example flash memory 18' and SDRAM 19'.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform total chlorine measurement of a sample of seawater.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring monochloramine in a seawater sample, the method comprising:
   introducing a thiocarbamate-based indicator and an iodide additive to the seawater sample to provide a mixture, measuring an intensity of fluorescence of the mixture; and
   determining an amount of monochloramine in the seawater sample based on the intensity of the fluorescence.

2. The method of claim 1, wherein the thiocarbamate-based indicator comprises a thiocarbamate derivative of hydroxyl coumarin.

3. The method of claim 2, wherein the thiocarbamate-based derivative is a derivative of 7-hydroxy-coumarin.

4. The method of claim 1, wherein the iodide additive is potassium iodide.

5. The method of claim 1, wherein the intensity of the fluorescence is correlated to a concentration of total chlorine in the seawater sample.

6. The method of claim 1, wherein the seawater sample comprises water from a ballast water system.

7. The method of claim 1, further comprising addition of a co-solvent.

8. The method of claim 7, wherein the co-solvent is selected from the group consisting of: poly(ethylene glycol), poly(ethylene glycol)dimethyl ether, and poly(ethylene glycol)methyl ether.

* * * * *